United States Patent
Yavitz

[11] Patent Number: 5,820,624
[45] Date of Patent: Oct. 13, 1998

[54] SYSTEM FOR ALTERING CORNEAL TISSUE

[75] Inventor: Edward Q. Yavitz, Rockford, Ill.

[73] Assignee: Quadrivium, L.L.C., Phoenix, Ariz.

[21] Appl. No.: 852,360

[22] Filed: May 7, 1997

Related U.S. Application Data

[63] Continuation-in-part of Ser. No. 503,101, Jul. 17, 1995, Pat. No. 5,649,922.

[51] Int. Cl.⁶ ................................................. A61B 17/36
[52] U.S. Cl. ................................................................. 606/4
[58] Field of Search ............................. 606/1, 4, 5, 6, 606/10, 11, 14

[56] References Cited

U.S. PATENT DOCUMENTS

| | | |
|---|---|---|
| 3,074,407 | 1/1963 | Moon et al. . |
| 4,156,124 | 5/1979 | Macken et al. . |
| 4,406,285 | 9/1983 | Villasenor et al. . |
| 4,461,294 | 7/1984 | Baron . |
| 4,840,175 | 6/1989 | Peyman . |
| 4,903,695 | 2/1990 | Warner et al. . |
| 4,905,711 | 3/1990 | Bennet et al. . |
| 4,976,709 | 12/1990 | Sand . |
| 5,057,104 | 10/1991 | Chess et al. . |
| 5,092,863 | 3/1992 | Schanzlin . |
| 5,108,412 | 4/1992 | Krumeich et al. . |
| 5,137,530 | 8/1992 | Sand . |
| 5,282,797 | 2/1994 | Chess . |
| 5,336,215 | 8/1994 | Hsueh et al. ................................ 606/4 |
| 5,356,409 | 10/1994 | Nizzola ....................................... 606/5 |
| 5,360,424 | 11/1994 | Klopotek .................................... 606/4 |
| 5,368,590 | 11/1994 | Itoh ............................................. 606/4 |
| 5,437,657 | 8/1995 | Epstein . |
| 5,486,172 | 1/1996 | Chess . |
| 5,582,608 | 12/1996 | Brown ....................................... 606/4 |
| 5,586,980 | 12/1996 | Kremer et al. ............................. 606/4 |
| 5,611,795 | 3/1997 | Slatkine et al. . |
| 5,616,139 | 4/1997 | Okamoto ................................... 606/4 |

FOREIGN PATENT DOCUMENTS

| | | |
|---|---|---|
| 0531756 | 3/1993 | European Pat. Off. . |
| WO92/01430 | 2/1992 | WIPO . |
| 92/10152 | 6/1992 | WIPO . |
| 94/18920 | 9/1994 | WIPO . |
| WO95/15134 | 6/1995 | WIPO . |

*Primary Examiner*—Jennifer Bahr
*Assistant Examiner*—Sonya Harris-Ogugua
*Attorney, Agent, or Firm*—Fletcher, Yoder & Edwards

[57] ABSTRACT

A system for treating vision disorders is disclosed. The system includes a heating device able to heat predetermined areas of the corneal tissue of an eye. The energy for heating is typically generated in the form of laser light or infrared that cause the tissue at that predetermined area to heat and shrink. The shrinkage shifts a plug or portion of the cornea with respect to the remainder of the eye to change the shape of the corneal surface and correct the problematic refractive error. A heat absorption modifier is used to avoid damage to the epithelial layer as energy is passed therethrough.

18 Claims, 3 Drawing Sheets

SYSTEM FOR ALTERING CORNEAL TISSUE

This is a continuation-in-part of U.S. patent application, Apparatus and Method for Altering Corneal Tissue, Ser. No. 08/503,101, filed on Jul. 17, 1995, now U.S. Pat. No. 5,649,922.

FIELD OF THE INVENTION

The present invention relates generally to a system for reshaping the cornea of an eye.

BACKGROUND OF THE INVENTION

Refractive errors such as nearsightedness and farsightedness can be reduced or corrected by reshaping the cornea of an eye. There are currently many methods for reshaping the cornea, including laser radial keratotomy and scalpel radial keratotomy. One problem with these procedures, particularly in correcting farsightedness, is the difficulty of gauging the effects of making incisions in the corneal surface.

One new technique involves heating the middle of the cornea in a radial pattern with a holmium laser. The heating causes the central cornea to bulge forward, thereby temporarily correcting for farsightedness. Unfortunately, the effect of the holmium laser alone is not permanent.

Moreover, it is difficult to contain the laser to only those areas that are to be heated. Most energy sources for providing heat, such as the holmium laser, pulsed infrared light sources and even low wavelength lasers having wavelengths on the order of 1320 nanometers, are absorbed first by the outermost epithelial layer of the cornea before reaching the inner layers of the cornea where the desired reshaping should occur. The absorption of energy by the epithelial layer causes damage to the epithelium that results in pain and permeability to bacteria. It would be advantageous to have a device and a method for permanently reshaping the cornea that guarantees precision in setting the diameter, centration and depth of the incision. It also would be advantageous to have a device and a method for permanently reshaping the cornea that guarantees precision in setting the diameter, centration and depth of the treatment while bypassing the epithelial layer. This latter type of intrastromal technique would permit modification of corneal curvature without incisions or removal of the epithelium or Bowman's membrane.

SUMMARY OF THE INVENTION

The present invention features a system for reshaping an area of corneal tissue about a pupil of an eye. The system comprises a fixture for treating a region of the epithelial layer of the eye to limit absorption of energy by the epithelium when light is passed through the region to a predetermined treatment area of corneal tissue. The system further includes a light emitter that may be oriented to direct light through the region to the predetermined treatment area of corneal tissue. The light is of sufficient intensity to heat the predetermined treatment area causing deformation of the corneal tissue.

According to another aspect of the invention, a system is provided for reshaping a predetermined area of corneal tissue of an eye that has an outer epithelial layer. The system comprises a heating device adapted to transfer energy to a predetermined area of corneal tissue until sufficient heating occurs to deform the corneal tissue. The system further includes a heat absorption modifier able to cooperate with the epithelial layer to limit heat buildup in the epithelial layer during heating of the predetermined area. The heat absorption modifier can be a cutter that is used to cut through the epithelial layer to permit transfer of energy, typically in the form of light, through the cut region and directly to the area of corneal tissue being treated. Alternatively, the heat absorption modifier can comprise a fixture designed for placement against the eye to act as a heat sink to eliminate heat buildup in the epithelial layer when energy is transferred through the epithelial layer. In another alternative embodiment, the heat absorption modifier includes a material that displaces the water in the epithelial layer to facilitate transfer of energy, such as laser light, through the epithelial layer without undue heating. The heating device may comprise a laser, such as a Nd:Yag laser, or an infrared light emitter, such as a pulsed infrared heat lamp.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENT

Figure 1:
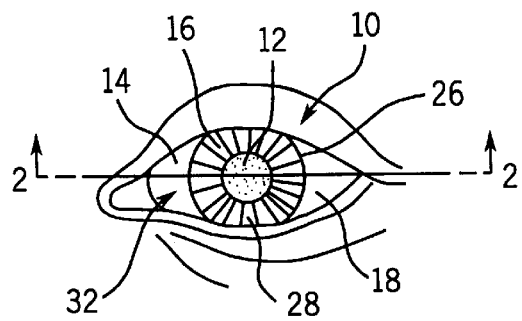
FIG. 1 is a front view of an eye that illustrates the cut portion of corneal tissue.

Referring generally to FIG. 1, an eye 10, such as a human eye, is disclosed. Eye 10 includes a pupil 12 surrounded by corneal tissue 14 and, for example, an iris 16. Corneal tissue 14 is bounded by a corneal surface 18.

Many vision disorders, such as nearsightedness and farsightedness, result from a slightly misshapen corneal surface 18. Theoretically, such disorders should be correctable by reshaping corneal surface 18 to compensate for the refractive errors causing the sight disorder. Practically, this may be accomplished according to the method and device described below.

Figure 2:
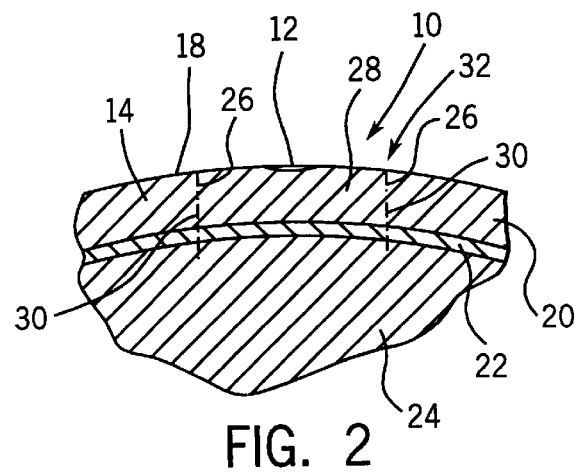
FIG. 2 is a cross-sectional view of FIG. 1 taken generally along line 2—2 of FIG. 1.

As illustrated in FIG. 2, eye 10, particularly corneal tissue 14, includes a plurality of layers between corneal surface 18 and a more central region of the eye that includes, for instance, the lens of the eye (not shown). An epithelium or epithelial layer 20 is bounded by corneal surface 18. Inwardly from epithelial layer 20 is a membrane layer 22, known as Bowman's membrane layer. Inwardly from membrane layer 22 is a collagen layer 24 that extends towards the center of the eye.

According to one embodiment of the present inventive method, a cut 26 is made into eye 10 through corneal surface 18, and preferably through epithelial layer 20 and membrane layer 22. Cut 26 is illustrated in FIGS. 1 and 2 and preferably extends substantially about pupil 12. According to one embodiment of the invention, cut 26 may be circular and extend in a circular pattern about pupil 12 at a given distance from pupil 12. Thus, cut 26 generally forms a plug portion 28 defined by an outer cut surface 30.

Figure 3A:
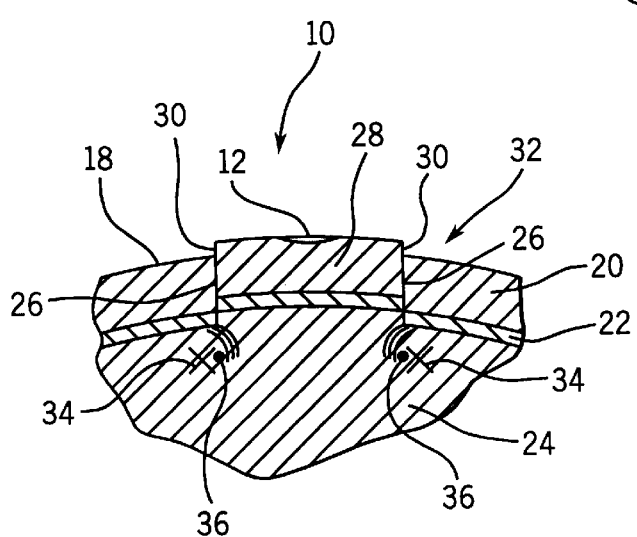
FIG. 3A is a cross-sectional view similar to that of FIG. 2 illustrating the corneal tissue after it has been treated.
Figure 3B:
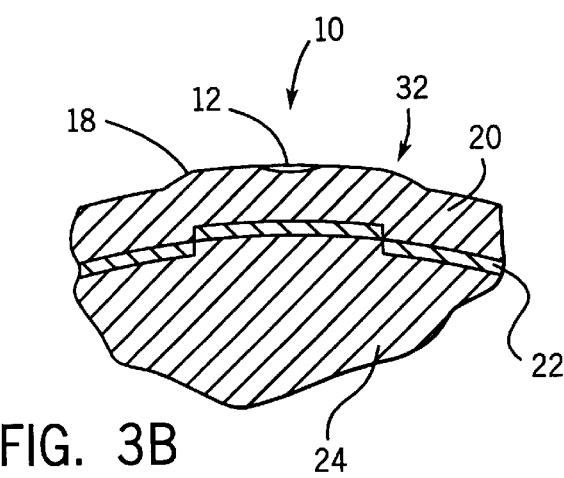
FIG. 3B is a cross-section view similar to that of FIG. 2 illustrating the corneal tissue after it has been treated and healed.

As illustrated in FIGS. 3A and 3B, a portion of the corneal tissue 14 may be deformed in a manner that moves plug portion 28 with respect to the remainder of the corneal tissue 14. Potentially, plug portion 28 can be moved inwardly with respect to eye 10 or outwardly with respect to the remainder of eye 10 as illustrated in FIG. 3A. Generally, plug portion 28 is moved slightly outwardly to correct refractive errors that lead to conditions such as hyperopia (farsightedness) or presbyopia.

As illustrated, plug portion 28 is cut from a predetermined region 32 of corneal tissue 14. By deforming a desired corneal portion 34, plug 28 is squeezed and moved slightly outwardly as illustrated in FIG. 3A. Cut 26 is then permitted to heal, thereby permanently affixing plug portion 28 in its new location with respect to the remainder of the corneal tissue 14, as illustrated in FIG. 3B.

To move plug portion 28 outwardly, it is preferred that corneal portion 34 be located proximate outer cut surface 30, preferably slightly outside and below outer cut surface 30 as indicated by each X in FIG. 3A. By shrinking this corneal portion 34 of corneal tissue 14, plug portion 28 is squeezed slightly outwardly to appropriately change the curvature of corneal surface 18. It should be noted that the necessary movement of plug portion 28 varies, depending on the type and severity of the vision disorder, but it is typically on the order of 20–80 microns. The movement illustrated in the Figures has been exaggerated merely for illustrative purposes. Also, corneal portion 34 may be within plug 28 if the desired motion of plug 28 is inward with respect to the surrounding corneal tissue. In either event. The displaced or separated intrastromal relationships recombine as the plug heals into place at its new location, thereby permanently changing the shape of the corneal surface.

The shrinking of corneal portion 34 and the consequent outward movement of plug portion 28 may be accomplished by selectively heating the corneal tissue at portion 34. Although the heating could be accomplished in a variety of ways, a laser of desired wavelength and intensity is preferably used. An example of one type of laser that has proved effective is a holmium laser. The laser energy causes corneal portion 34 of collagen layer 24 to shrink around plug portion 28 and force plug portion 28 outwardly. The effect of the laser may be enhanced by injecting a dye, such as the photodye Rose Bengal manufactured by Smith and Nephew of London, England, into the area of portion 34. Dye 36 may be injected either independently or at the time plug 28 is created by cut 26. In either event, the dye absorbs more of the laser energy creating a greater heating of region 34 with a lower energy laser. The lower energy laser tends to protect the surrounding corneal tissue. In some procedures, the laser may be of sufficiently low energy to avoid damaging the epithelium even when the epithelium is not cut and the light energy is transferred through the epithelium. This is particularly true when dye is injected at the desired area of treatment, e.g., corneal portion 34, to promote greater heating and deformation of corneal tissue at the area of treatment without changing the intact epithelial layer 20.

The epithelial layer 20 can be protected further by reducing the likelihood that the epithelium will absorb sufficient energy from the laser, infrared light source or other heat source to damage the epithelium when the energy is transferred therethrough. This can be accomplished, as explained more fully below, by physically cooling the epithelium as energy is directed to corneal portion 34. The epithelial layer 20 can also be protected by selectively removing the water ($H_2O$) from a portion of the epithelium and replacing them with a chemical that does not absorb heat energy from the laser, infrared heat lamp or other energy source.

Preferably, the laser light energy is split into multiple beams of light, e.g., eight, which are evenly spaced about plug 28 to cause uniform, simultaneous deformation of corneal tissue. It is also preferred that the heating be accomplished at the same time or shortly after plug 28 is cut to avoid swelling, hydration and detrimental changes to the cut corneal tissue.

Figure 4:
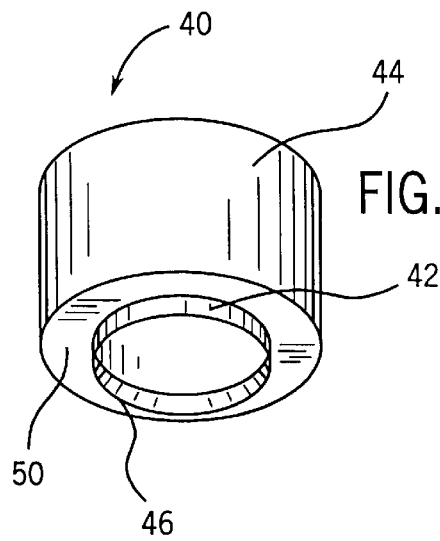
FIG. 4 is a perspective representation of a cutting device according to a preferred embodiment of the invention.
Figure 5:
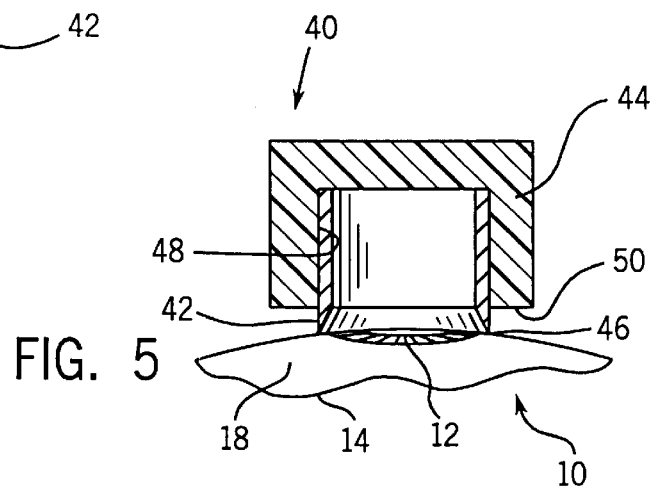
FIG. 5 is a cross-sectional view of the device illustrated in FIG. 4 and disposed adjacent an eye.

Referring generally to FIG. 4, an apparatus 40 for reshaping predetermined region 32 of corneal tissue 14 is illustrated. Apparatus 40 includes a cutter 42 and a guard 44. Cutter 42 is preferably a blade, such as a trephine blade made from an appropriate metal, such as surgical steel. Cutter 42 is mounted to guard 44 and includes a cutting edge 46 (See FIGS. 4 and 5) designed preferably to cut substantially about the perimeter of pupil 12 at a given radius to create plug 28. In the most preferred embodiment, cutting edge 46 has a generally circular configuration.

Guard 44 preferably has a hollow interior 48 designed to receive cutter 42. The exact configuration can vary substantially without departing from the scope of the present invention, and cutter 42 may be fixedly mounted or adjustably mounted to permit retraction of cutting edge 46 into guard 44. However, during the cutting operation illustrated in FIG. 5, cutting edge 46 is maintained at a predetermined distance from a leading edge 50 of guard 44. Thus, cutting edge 46 should remain fixed with respect to leading edge 50 during the cutting operation. In some applications, the distance between leading edge 50 and cutting edge 46 may vary at different points, but the predetermined distance at each point remains the same during the cutting operation.

Cutting edge 46 extends at least 50 microns and up to 800 microns from leading edge 50. Typically, cutting edge 46 extends at least 50 microns and up to 200 microns. The exact distance is determined according to the type of vision disorder and the severity of that disorder. If a laser is used to cut the corneal tissue, the predetermined distance can precisely be controlled by controlling the intensity of the laser.

In the FIGS., cutter 42 is exemplified by a circular trephine cutter, but a variety of cutters could be used. For example, certain lasers could potentially be used to provide cut 26 and create plug 28. An example is an excimer laser, such as those manufactured by the Laser Sight Company of Orlando, Fla. Movable blades could also be used to create cut 26 either fully or partially about the perimeter of pupil 12.

Figure 6:
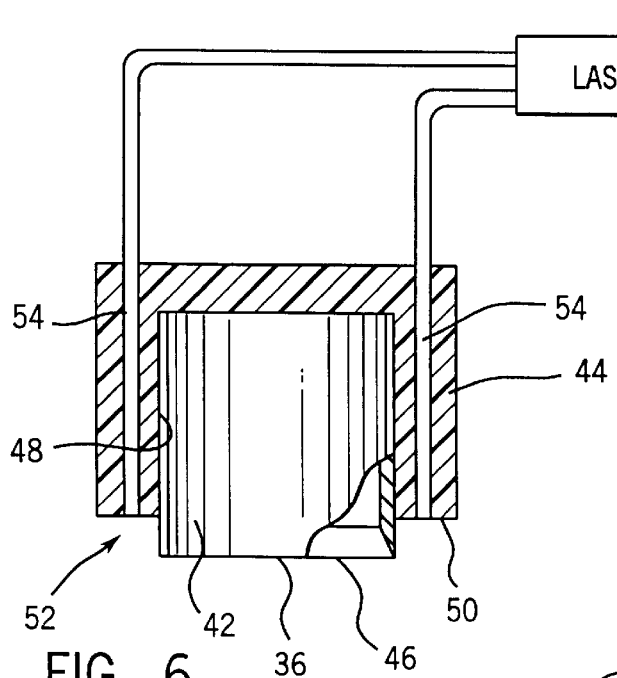
FIG. 6 is a side view of another exemplary device used for cutting and altering corneal tissue.
Figure 7:
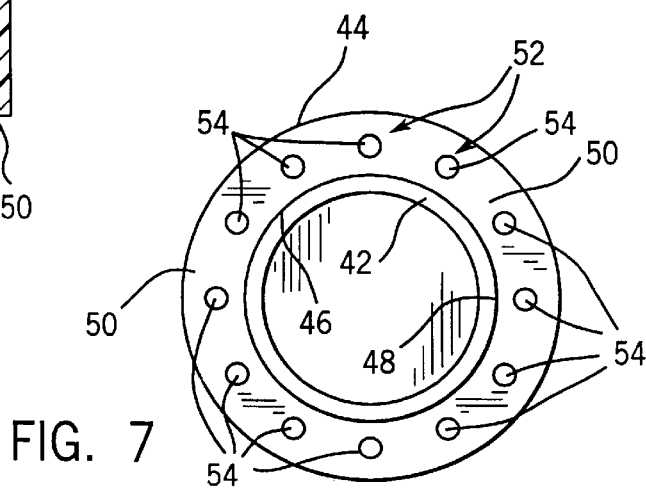
FIG. 7 is a bottom view of the device illustrated in FIG. 6.

As illustrated in FIGS. 6 and 7, guard 44 may incorporate a light transmitting material 52 capable of transmitting laser light energy through guard 44 and towards corneal portion 34 of tissue 14, preferably through cut 26. Light transmitting material 52 may be made of a variety of materials, such as quartz, sapphire or optical fibers 54, as illustrated in FIGS. 6 and 7. Optical fibers 54 are oriented to direct laser light energy, supplied by a laser light source 56, to corneal portion 34 of tissue 14. An exemplary laser is a holmium laser, such as those manufactured by Sunrise Corp. of Calif. or Summit Corp. of Mass.

In the illustrated embodiment, the light transmitting material 52 extends through guard 44 and is uniformly disposed about leading edge 50 to provide a transfer of energy that heats corneal portion 34 in an evenly distributed manner about the circumference of plug 28. Thus, the heating of portion 34 is uniform, causing a uniform shrinking of the collagen layer proximate plug 28 to thereby precisely move plug 28 outwardly the desired amount.

Optionally, dye 36 may be coated on cutter 42 along cutting edge 46 to dye the corneal tissue disposed in proximity to plug 28 as cutter 42 is pressed into eye 10. As explained above, dye 36 more readily absorbs the laser light energy to provide heating, and consequent shrinking, of the collagen layer proximate plug 28. This permits the use of a lower energy laser that is less likely to harm or affect tissues other than those proximate plug 28.

As described above, cutter 42 works as a heat absorption modifier by cutting or severing the epithelial layer 20 to permit energy to be transferred to an intrastromal region, such as corneal portion 34, without passing directly through the epithelium. However, in some applications it may be advantageous to leave the epithelium intact. Avoiding cutting of epithelial layer 20 can, among other things, reduce the pain to the patient, reduce the healing time and limit the threat of infection. However, a different type of heat absorption modifier is required to avoid damage to epithelial layer 20, e.g., by excess heating, when energy is passed through the epithelium to Bowman's membrane layer 22 or other intrastromal regions, such as corneal portion 34. In some procedures, the combination of a low energy source, such as a low energy laser, can be combined with the injection of dye 36 into corneal portion 34. In these procedures, sufficient energy can be passed through epithelial layer 20 to be absorbed by dye 36 at corneal portion 34. The absorption of energy by the dye provides sufficient heating to obtain the desired deformation of corneal tissue at corneal portion 34.

Figure 8:
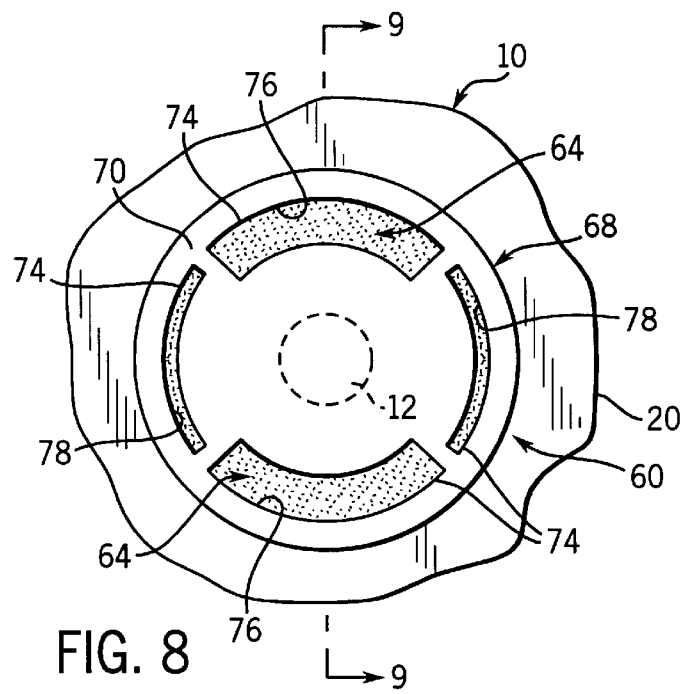
FIG. 8 is a front view of an eye with an alternate heat absorption modifier.
Figure 9:
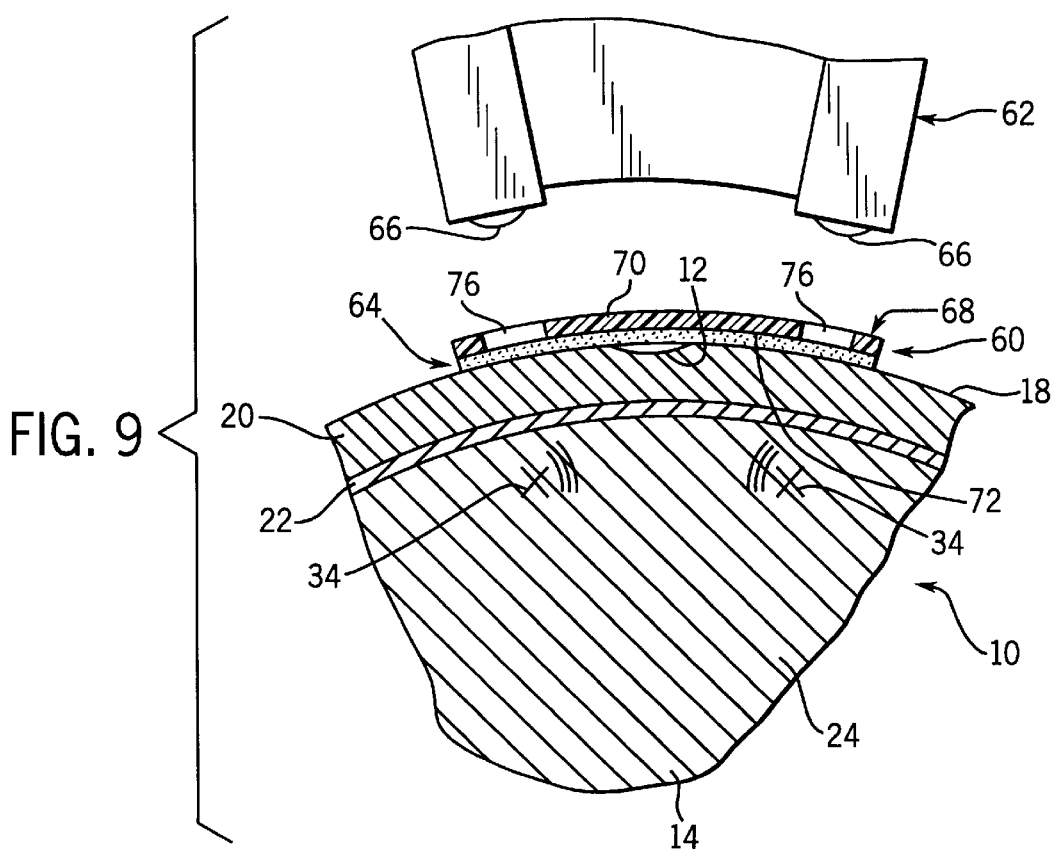
FIG. 9 is a cross-sectional view taken generally along line 9—9 of FIG. 8 and also showing a heater device according to one embodiment of the invention.

However, it is typically necessary to provide an additional heat absorption modifier. As illustrated in FIGS. 8 and 9, an alternate heat absorption modifier 60 can be used in combination with a heating device 62.

In one embodiment of heat absorption modifier 60, a material 64 is placed against the outer surface of epithelial layer 20. Material 64 may include an appropriate isotope, preferably in liquid form, that is formulated to displace the water ($H_2O$) in epithelial layer 20. The displacement of water limits the epithelial layer's absorption of certain types of energy emitted from heating device 62 and passed through epithelial layer 20 to a predetermined treatment area of corneal tissue, such as corneal portion 34. Exemplary materials 64 are deuterium oxide ($D_2O$) or tritium oxide ($H_3O$). When such materials are used, energy may be emitted from heating device 62 in the form of laser light or infrared. Heating device 62 typically is of the type that emits energy via one or more energy emitters 66, e.g. light emitters, which direct energy through epithelial layer 20 to predetermined treatment area 34. For example, heating device 62 may comprise a Nd:Yag laser having a wavelength of approximately 1320 nanometers or it can be a pulsed infrared heat lamp. The intensity of the energy emitted will depend on the type of procedure and the amount of corneal tissue deformation required for the correction of eye 10.

As illustrated, material 64 is preferably combined with or formed as part of a fixture 68. Fixture 68 includes a guard portion 70 that has an inner contoured surface 72 configured to generally match the contour of outer surface 18 of eye 10. Guard portion 70 may be formed similarly to a soft contact lens and be made from materials such as methaphilcon or viflicon. Guard portion 70 is able to help hold material 64 against epithelial layer 20 as material 64 is absorbed by epithelial layer 20 to displace the water within the epithelial layer 20, at least in the regions of the epithelium through which energy from heating device 62 will pass.

In the illustrated embodiment, guard portion 70 is shown as separate from heating device 62, however, guard portion 70 can also be constructed as an integral part with or mounted to heating device 62 to ensure proper centration and registration with the patient's eye 10. Additionally, guard portion 70 preferably includes one or more fenestrations 74 that permit energy from heating device 62 to freely pass through guard portion 70. The use of guard portion 70 also allows treatment of the patient's eye 10 to be customized to the patient's cornea. Fenestrations 74 can be asymmetric openings for the treatment of astigmatism and other irregularities of the cornea curvature by allowing more shrinkage along one axis versus another axis. For example, as illustrated best in FIG. 8, fenestrations 74 may include a pair of wider openings 76 and a pair of narrower openings 78. Thus, more energy from heating device 62 is allowed to freely pass through wider openings 76 to the desired treatment area, e.g. portion 34, than through narrower openings 78, thereby causing greater shrinkage of tissue along the ninety degree axis than along the one hundred eighty degree axis.

It should also be noted that with some procedures it may be possible to avoid problematic damage to epithelial layer 20 without the use of deuterium oxide or tritium oxide. For example, a liquid, such as water, in combination with guard portion 70 also acts as a heat sink for energy otherwise absorbed by epithelial layer 20 as that energy passes through the epithelium to the desired area of treatment, e.g., corneal portion 34. For example, guard portion 70 in combination with a heat dissipating liquid can absorb sufficient heat from epithelial layer 20 if a low energy laser is passed through the epithelium to the predetermined treatment area of corneal tissue. In this type of procedure, energy is still absorbed by epithelial layer 20 but guard portion 70 along with the heat dissipating liquid (if necessary), are able to absorb heat from epithelial layer 20 at a sufficient rate to avoid damage to the epithelium.

It will be understood that the foregoing description is of a preferred exemplary embodiment of this invention and that the invention is not limited the specific forms shown. For example, the cutter may comprise a solid metal material, other solid materials, a laser or a variety of other cutting devices able to penetrate corneal tissue. The shape of any solid blade may be circular, oval, or otherwise shaped, depending on the desired type of plug to be moved with respect to the remainder of the eye. The deformation of the corneal tissue may be accomplished in a variety of ways including heating, chemical action, or other suitable procedures to cause the desired shrinkage or expansion of the tissue that adjusts the position of the plug. Also, the use of a water displacement material can be combined with an appropriate dye injected at the area of treatment or a cutter can be used to cut the plug in combination with the use of a water displacement material placed against the epithelial layer. These and other modifications may be made in the design and arrangement of the elements without departing from the scope of the invention as expressed in the appended claims.

What is claimed is:

1. A system for reshaping an area of corneal tissue about a pupil of an eye, the system comprising:

a fixture for treating a region of the epithelial layer of the eye to limit the absorption of energy by the region when light is passed through the region to a predetermined treatment area of corneal tissue; and an energy emitter that may be oriented to direct energy through the region to the predetermined treatment area of corneal tissue, the energy being of sufficient intensity to heat the predetermined treatment area causing deformation of the corneal tissue.

2. The system as recited in claim 1, wherein the energy emitter comprises a laser.

3. The system as recited in claim 2, wherein the laser is an Nd:Yag laser.

4. The system as recited in claim 1, wherein the energy emitter comprises a pulsed infrared lamp.

5. The system as recited in claim 1, wherein the fixture is contoured to rest against an outside surface of the epithelial layer.

6. The system as recited in claim 5, wherein the fixture includes at least one fenestration through which the light passes prior to entering the region.

7. The system as recited in claim 1, wherein the energy emitter comprises a laser.

8. The system as recited in claim 7, wherein the laser is an Nd:Yag laser.

9. The system as recited in claim 1, wherein the energy emitter comprises an infrared emitter.

10. The system as recited in claim 1, wherein the water displacement materials comprises deuterium oxide.

11. The system as recited in claim 1, wherein the water displacement material comprises tritium oxide.

12. The system for reshaping a predetermined area of corneal tissue of an eye having an epithelial layer, the system comprising:

a heating device adapted to transfer energy to a predetermined area of corneal tissue until sufficient heating occurs to deform the corneal tissue; and a heat absorption modifier able to cooperate with the epithelial layer to limit heat buildup in the epithelial layer during heating of the predetermined area wherein the heat absorption modifier comprises an isotopic material that displaces the water naturally occurring in the epithelial layer to facilitate transfer of the energy therethrough.

13. The system as recited in claim 12, wherein the heat absorption modifier comprises a cutter capable of creating a cut into the epithelium through which the energy is transferred to the predetermined area substantially without passage through the epithelial layer.

14. The system as recited in claim 12, wherein the heat absorption modifier comprises a fixture that may be placed against the eye to act as a heat sink.

15. The system as recited in claim 12, wherein the material includes deuterium oxide.

16. The system as recited in claim 12, wherein the material includes tritium oxide.

17. The system as recited in claim 12, wherein the heating device comprises a laser.

18. The system as recited in claim 12, wherein the heating device comprises an infrared lamp.

* * * * *

UNITED STATES PATENT AND TRADEMARK OFFICE
CERTIFICATE OF CORRECTION

PATENT NO. : 5,820,624
DATED : October 13, 1998
INVENTOR(S) : Edward Q. Yavitz

It is certified that error appears in the above-identified patent and that said Letters Patent is hereby corrected as shown below:

Claim 1, at the end, the following should be inserted:

-- wherein the fixture included an isotopic water displacement material for transfer to the region of the epithelial layer, where upon transfer, the isotopic water displacement material displaces water naturally occurring in the epithelial layer form the region--.

Signed and Sealed this

Twenty-first Day of September, 1999

*Attest:*

Q. TODD DICKINSON

*Attesting Officer*     *Acting Commissioner of Patents and Trademarks*